United States Patent
Koenig et al.

(10) Patent No.: US 6,764,988 B2
(45) Date of Patent: Jul. 20, 2004

(54) SKIN CLEANSING COMPOSITION INCORPORATING ANIONIC PARTICLES

(75) Inventors: David William Koenig, Menasha, WI (US); Beth Anne Lange, Appleton, WI (US); Bernard J. Minerath, Oshkosh, WI (US); Bruce Scott Williamson, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 127 days.

(21) Appl. No.: 09/837,628

(22) Filed: Apr. 18, 2001

(65) Prior Publication Data

US 2002/0183216 A1 Dec. 5, 2002

(51) Int. Cl.$^7$ ................................................. C11D 3/22
(52) U.S. Cl. ....................... 510/130; 510/138; 510/139; 510/471
(58) Field of Search .................................. 510/130, 138, 510/139, 471

(56) References Cited

U.S. PATENT DOCUMENTS

| | | |
|---|---|---|
| 3,594,221 A | 7/1971 | Baldwin |
| 3,804,092 A | 4/1974 | Tunc |
| 3,875,141 A | 4/1975 | Drisch |
| 4,044,766 A | 8/1977 | Kaczmarzyk et al. |
| 4,100,324 A | 7/1978 | Anderson et al. |
| 4,234,652 A | 11/1980 | Vanoni et al. |
| 4,273,118 A | 6/1981 | Smith |
| 4,289,824 A | 9/1981 | Smith |
| 4,401,712 A | 8/1983 | Morrison |
| 4,405,324 A | 9/1983 | Cruz, Jr. |
| 4,430,381 A | 2/1984 | Harvey et al. |
| 4,468,428 A | 8/1984 | Early et al. |
| 4,543,410 A | 9/1985 | Cruz, Jr. |
| 4,587,154 A | 5/1986 | Hotchkiss et al. |
| 4,643,939 A | 2/1987 | Sugiyama et al. |
| 4,684,570 A | 8/1987 | Malaney |
| 4,738,847 A | 4/1988 | Rothe et al. |
| 4,740,398 A | 4/1988 | Bouchette |
| 4,744,933 A | 5/1988 | Rha et al. |
| 4,772,501 A | 9/1988 | Johnson et al. |
| 4,822,620 A | 4/1989 | Chamberlain et al. |
| 4,931,201 A | 6/1990 | Julemont |
| 5,087,450 A | 2/1992 | Lister |
| 5,122,598 A | 6/1992 | della Valle et al. |
| 5,169,712 A | 12/1992 | Tapp |
| 5,264,269 A | 11/1993 | Kakiuchi et al. |
| 5,429,854 A | 7/1995 | Currie et al. |
| 5,436,066 A | 7/1995 | Chen |
| 5,458,963 A | 10/1995 | Meirowitz et al. |
| 5,466,461 A | 11/1995 | della Valle et al. |
| 5,500,068 A | 3/1996 | Srinivasan et al. |
| 5,501,772 A | 3/1996 | Elliott et al. |
| 5,501,773 A | 3/1996 | Elliott et al. |
| 5,558,861 A | 9/1996 | Yamanaka et al. |
| 5,567,277 A | 10/1996 | Elliott et al. |
| 5,647,956 A | 7/1997 | Elliott et al. |
| 5,679,877 A | 10/1997 | Erilli et al. |
| 5,702,992 A | 12/1997 | Martin et al. |
| 5,728,824 A | 3/1998 | Narayan et al. |
| 5,783,502 A | 7/1998 | Swanson |
| 5,786,282 A | 7/1998 | Carter et al. |
| 5,810,797 A | 9/1998 | Menard et al. |
| 5,817,381 A | 10/1998 | Chen et al. |
| 5,817,801 A | 10/1998 | Boerstoel et al. |
| 5,888,524 A | 3/1999 | Cole |
| 5,932,158 A | 8/1999 | Boerstoel et al. |
| 5,948,710 A | 9/1999 | Pomplun et al. |
| 6,001,819 A | 12/1999 | Simon et al. |
| 6,002,064 A | 12/1999 | Kobylivker et al. |
| 6,083,582 A | 7/2000 | Chen et al. |
| 6,111,060 A | 8/2000 | Gruber et al. |
| 6,183,766 B1 * | 2/2001 | Sine et al. ............... 424/405 |
| 6,280,758 B1 * | 8/2001 | Warren et al. ........... 424/404 |
| 6,344,218 B1 * | 2/2002 | Dodd et al. ............. 424/605 |
| 6,436,885 B2 * | 8/2002 | Biedermann et al. ....... 510/131 |

FOREIGN PATENT DOCUMENTS

| | | |
|---|---|---|
| EP | 0557577 A1 | 9/1992 |
| EP | 0557577 B1 | 9/1992 |
| EP | 950391 * | 10/1999 |
| EP | 0950391 A1 | 10/1999 |
| EP | 1215276 A1 | 6/2002 |
| JP | 06-227284 * | 3/1996 |
| JP | 08-067622 | 3/1996 |
| JP | 11-100598 | 4/1999 |
| JP | 2002-275050 | 9/2002 |
| WO | WO 97/01660 | 1/1997 |
| WO | WO 97/12917 | 4/1997 |
| WO | WO 97/28214 | 8/1997 |
| WO | WO 98/59100 | 12/1998 |
| WO | WO 00/05310 | 2/2000 |
| WO | WO 01/078659 A1 | 10/2001 |

OTHER PUBLICATIONS

PCT/US02/12515 PCT International Search Report completed Dec. 13, 2002.

* cited by examiner

*Primary Examiner*—Charles Boyer
(74) *Attorney, Agent, or Firm*—Senniger, Powers, Leavitt & Roedel (57) ABSTRACT

Novel skin cleansing formulations are disclosed herein. The formulations comprise an anionic particles, microfibers, or compounds which dislodge contaminants from skin through electrostatic interactions. The anionic particles, compounds, or microfibers can easily be incorporated into various products for improved skin cleaning and removal of the contaminant from the skin. The anionic particles do not necessarily kill microbes on the skin, but dislodge them from the skin surface such that they and other contaminants can easily be removed away from the skin by a substrate.

76 Claims, 3 Drawing Sheets

SKIN CLEANSING COMPOSITION INCORPORATING ANIONIC PARTICLES

BACKGROUND OF THE INVENTION

The present invention relates to skin cleansing compositions. More particularly, the present invention relates to skin cleansing compositions effective against a broad range of soils and microorganisms such as bacteria, fungi, yeast, molds, protozoan, and viruses. The skin cleansing compositions of the present invention, which can be incorporated into various products such as wet wipes, lotions, soaps, tampons, facial tissue, bath tissue etc. incorporate anionic particles or microfibers, such as carboxymethylcellulose microfibers, which have an effective charge density of from about 0.1 microequivalents/g to about 500 milliequivalents/g, or more. When the cleansing composition contacts the skin, the anionic particles or microfibers contained within the cleansing composition contact the skin and contaminants and dislodge the contaminants from the skin. In some embodiments, the cleansing composition can be utilized in combination with a substrate such that when the contaminant is dislodged from the skin, it is bound to the substrate and removed from the skin surface.

The skin is the largest organ of the human body. As a boundary layer, the skin performs several major functions: it maintains the body at a correct temperature, holds in essential fluids, and protects against toxic agents, microorganisms, and the sun's potentially harmful rays. Proper skin maintenance is essential for good health. For most people, proper skin maintenance begins with daily cleansing.

Human skin is exposed to various contaminants daily through both contacts with various biological fluids such as urine and feces as well as contact with numerous environmental factors. Examples of contaminants that the skin contacts everyday include both gram negative and gram positive bacteria, yeast, fungi, mold, protozoan and viruses. Although most microbes are negatively charged due to their chemistry and structures, they can adhere to skin, which is also typically negatively charged, through electrostatic interactions, hydrophobic interactions and ligand interactions. Although these attachment mechanisms are not completely understood, their cumulative effect can tightly bind numerous microbes such as *Candida albicans* to skin resulting in inflammation, irritation and/or infection. Further, numerous other microbes, microbial metabolic products, and inorganic debris also contact and foul skin on a daily basis.

The above-listed contaminants, as well as numerous others, are often irritating to the skin and can initiate an elaborate cascade of immunological events upon contact with skin cells. Ultimately, these events may lead to severe skin irritation, inflammation, and even infection. Skin cleaning on a daily basis can prevent or minimize skin irritation and inflammation caused by the immunological events.

Conventionally, cleaning of the skin has included any activity that kills, binds and/or removes contaminants present on the skin's surface. Traditionally, skin cleaning has been accomplished through the use of compositions such as solution-based skin cleaning products, bath tissues, facial tissues, and wet wipes. Wet wipes are especially preferred by many for cleaning of urine and fecal material from babies or elderly adults. Most wet wipes commercially available contain microbiocidal agents that are typically highly effective against numerous microbes.

Microbiocidal agents contained in many wet wipes and other cleaning agents may, however, irritate the skin of some users due to the potentially harsh chemicals utilized to provide the antimicrobial effect. As such, although wet wipes are generally effective in cleaning and maintaining healthy skin, some wet wipes may be unsuitable for use by some people. Some wet wipes utilized contain harsh surfactants and/or alcohol or other additives which, while effective against numerous microbes, may dry out or chafe skin. Further, use of microbiocidal agents contained in many wet wipes around open wounds is generally discouraged as the killed microbes may cause further inflammation if they enter the open wounds. Therefore, a need exists in the art for alternative cleaning methods that do not irritate, chafe, or otherwise damage the skin of the user. Further, a need exists for alternative cleaning methods that simply remove microbes and soil from the skin surface without killing the microbes and risking further infection of open wounds.

SUMMARY OF THE INVENTION

The present invention provides a cleansing formulation, a method of using the cleansing formulation, and products incorporating the cleansing formulation. The cleansing formulation of the present invention is highly effective in dislodging numerous bacteria, fungi, yeast, molds, protozoan, viruses, soils, and other substances from the skin's surface. The cleansing formulations of the present invention do not necessarily kill the microbes on the skin's surface. The cleanser will dislodge the microbes or other contaminants through electrostatic interactions between the skin surface and contaminant. Release of the contaminant allows for removal from the surface of the skin. It has been discovered that by providing a cleansing solution comprising anionic particles or microfibers having an effective charge density of from about 0.1 microequivalents/g to about 500 milliquivalents/g or more, numerous microbes can be electrostatically dislodged from the skin's surface and ultimately be removed. The anionic particle-containing cleansing solutions of the present invention, which may be used in combination with a wet wipe, for example, are safe for use around wounds in the skin as microbes are removed from the skin surface without a substantial risk of rupturing and thus the risk of introduction of byproducts from the microbe into wounds is minimized or eliminated.

Briefly, therefore, the present invention is directed to a wet wipe comprising a fibrous sheet material and a cleansing solution capable of dislodging contaminants from skin. The cleansing solution comprises from about 0.001 mg/(mL of cleansing solution) to about 10 mg/(mL of cleansing solution) of anionic particles having a diameter of from about 0.1 micrometers to about 10 micrometers and an effective charge density of from about 0.1 microequivalents/g to about 500 milliequivalents/g.

The invention is further directed to a wet wipe comprising a fibrous sheet material and a cleansing solution capable of dislodging contaminants from skin. The cleansing solution has a pH of from about 2 to about 9 and comprises from about 0.001 mg/(mL of cleansing solution) to about 10 mg/(mL of cleansing solution) of anionic particles having a diameter of from about 0.1 micrometers to about 10 micrometers and an effective charge density of from about 0.1 microequivalents/g to about 500 milliequivalents/g.

The invention is further directed to a cleansing solution suitable for direct application to skin capable of dislodging contaminants from skin. The cleansing solution comprises from about 0.001 mg/(mL of cleansing solution) to about 10 mg/(mL of cleansing solution) of anionic particles having a diameter of from about 0.1 micrometers to about 10 micrometers and an effective charge density of from about 0.1 microequivalents/g to about 500 milliequivalents/g.

The invention is further directed to a cleansing solution suitable for direct application to skin capable of dislodging contaminants from skin. The solution has a pH of from about 2 to about 9 and comprises from about 0.001 mg/(mL of cleansing solution) to about 10 mg/(mL of cleansing solution) of anionic particles having a diameter of from about 0.1 micrometers to about 10 micrometers and an effective charge density of from about 0.1 microequivalents/g to about 500 milliequivalents/g.

The invention is further directed to a product comprising a substrate comprising anionic particles capable of dislodging contaminants from skin. The substrate comprises from about 0.001 mg/(g of substrate) to about 10 mg/(g of substrate) of anionic particles having a diameter of from about 0.1 micrometers to about 10 micrometers and an effective charge density of from about 0.1 microequivalents/g to about 500 milliequivalents/g.

Other objects and features of this invention will be in part apparent and in part pointed out hereinafter.

DEFINITIONS

Within the context of this specification, each term or phrase below will include, but not be limited to, the following meaning or meanings:

(a) "Anionic Particle" refers to a particle which increases the overall negative charge of a cleansing composition.

(b) "Bonded" refers to the joining, adhering, connecting, attaching, or the like, of two elements. Two elements will be considered to be bonded together when they are bonded directly to one another or indirectly to one another, such as when each is directly bonded to intermediate elements.

(c) "Contaminant" refers to soils, microbes, gram positive and gram negative bacteria, yeast, viruses, feces, urine, menses, enzymes, toxins, endotoxins, blood, protozoan, organic and inorganic materials and other organic and inorganic soils.

(d) "Film" refers to a thermoplastic film made using a film extrusion and/or foaming process, such as a cast film or blown film extrusion process. The term includes apertured films, slit films, and other porous films, which constitute liquid transfer films, as well as films which do not transfer liquid.

(e) "Layer" when used in the singular can have the dual meaning of a single element or a plurality of elements.

(f) "Meltblown" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers, which may be continuous or discontinuous, are generally smaller than about 0.6 denier, and are generally self bonding when deposited onto a collecting surface. Meltblown fibers used in the present invention are preferably substantially continuous in length.

(g) "Nonwoven" refers to materials and webs of material which are formed without the aid of a textile weaving or knitting process.

(h) "Particle" refers to particles, fibers, microfibers, compounds and combinations and mixtures thereof.

(i) "Polymeric" includes, but is not limited to, homopolymers, copolymers, such as for example, block, graft, random and alternating copolymers, terpolymers, etc. and blends and modifications thereof. Furthermore, unless otherwise specifically limited, the term "polymeric" shall include all possible geometrical configurations of the material. These configurations include, but are not limited to, isotactic, syndiotactic and atactic symmetries. These polymers can be petroleum based, synthetic, natural, cellulosic, or other polymers.

(j) "Thermoplastic" describes a material that softens when exposed to heat and which substantially returns to a nonsoftened condition when cooled to room temperature.

DETAILED DESCRIPTION OF THE PREFERRED EMBODIMENTS

In accordance with the present invention, it has been discovered that numerous contaminants such as, for example, *Candida albicans*, attached to the skin can be effectively dislodged from the skin's surface through the use of a cleansing composition or product comprising a suitable amount of anionic particles, such as, for example, carboxymethylcellulose microfibers, having a suitable effective charge density or cation exchange capacity. The cleansing compositions of the present invention can easily be used in combination with a substrate that binds the contaminants dislodged from the skin and removes the contaminants away from the skin surface. Surprisingly, the cleansing compositions of the present invention are highly effective in removing contaminants from the skin yet are very gentle and non-irritating to the skin. Advantageously, the cleansing compositions of the present invention do not necessarily kill cells or puncture cell walls but simply dislodge the contaminant from the skin surface allowing subsequent removal. By facilitating the release and binding of skin contaminants, the formulations and substrates of the present invention significantly improve skin health.

It is typically preferred that the anionic particles and/or microfibers used in the formulations of the present invention are present in a hydrated environment on the skin surface for maximum effectiveness. When the cleansing formulations incorporating the anionic particles and/or microfibers are incorporated into a wet wipe or similar wipe, or into a lotion, for example, the anionic particles and/or microfibers are typically incorporated into the wetting solution in the wet wipe or directly into the lotion, which are hydrous environments. The anionic particles and/or microfibers, as discussed below, can also be incorporated into dry substrates such as facial or bath tissue, for example, in accordance with the present invention. Although present on the facial or bath tissue in a "dry" form, once the facial or bath tissue is used, the secretions or excretions being cleaned act to hydrate the environment surrounding the anionic particles and/or microfibers and allow the required interactions between the anionic particles, contaminants and the skin to occur such that the contaminants can be dislodged from the skin.

The cleansing formulations of the present invention contain anionic particles, microfibers or compounds that electrostatically interact with contaminants such as gram positive and gram negative bacteria, fungi, yeast, molds, protozoan, viruses and other soils and inorganic particles and dislodge the contaminant from the skin's surface so that a substrate used in combination with the cleansing formulation may bind and carry away the contaminant.

The anionic particles used in the formulations do not necessarily kill or inhibit the growth of microbes, but displace the predominantly negatively charged microbes or other contaminants from the skin surface through electrostatic interactions and repulsions such that they may be carried away. This is highly advantageous in that the cleansing formulations of the present invention do not require an antimicrobial agent to be highly effective. When the cleansing formulations of the present invention are utilized in or around skin wounds, microbes are not simply killed and left on the skin, but can actually be removed away from the skin. This may reduce the chance of further infection in and around the wound. Further, the anionic particles used in the formulations of the present invention are substantially non-toxic and non-irritating to the skin.

Without being bound to a particular theory, it appears that by increasing the repulsive forces between the anionic particle, such as a carboxymethylcellulose microfiber, and the contaminant on the skin's surface in excess of the forces attracting the contaminant to the skin, cleaning of the skin can be significantly enhanced by dislodging the contaminant. It appears that the anionic particles interact with the overall net negative charge of the skin causing the detachment of the contaminant from the skin through an electrostatic interaction. The interaction between the anionic particles and the skin appears to be stronger than the combined forces of adhesion that retain the contaminant on the skin including hydrophobic interactions, electrostatic interactions, and ligand interactions. Because the contaminant is released from the skin by the charge-modified cleansing solution, it may be easily and efficiently carried away by a substrate containing the cleansing formulation. This is highly advantageous over more traditional cleaning formulations as the contaminant is not merely dislodged from the skin surface, but is first dislodged and then removed from the skin's surface through interactions with a substrate containing the anionic particles. This action also aids in precluding or minimizing the redeposition of the soil onto the skin surface.

An important novel aspect of the present invention is that the charge-modified cleansing formulations of the present invention significantly improve skin cleanliness and health without necessarily killing microorganisms present on the surface of the skin. As mentioned above, this can be a critical factor when cleansing solutions are utilized around wounds or are embodied in wound dressings or wound cleaning products. Typically, when antimicrobial agents, which are common in commercially available wet wipes, kill microorganisms, the outer wall of the microorganism is penetrated and opened to allow access by a killing agent such as, for example, an organic acid. Although this typically results in a kill of the microorganism, the inside contents of the microorganism can "spill out" into an open wound and lead to further complications or increased inflammation, irritation, and infections. This significant problem is minimized or eliminated by the present invention which releases the microorganism from the skin such that it can be transferred to a substrate surface and carried away. The interaction between microorganisms or other contaminants and the charge-altered cleansing compositions of the present invention results in an actual energy transfer, i.e., energy is released and recaptured in the dislodging and rebinding of contaminants from the skin surface to the cleaning substrate. This cleaning mechanism may also be important for the control of certain other skin problems, such as, for example, diaper rash.

The cleansing formulations of the present invention, which may be incorporated into "wet" applications such as a wet wipe or therapeutic skin cream, or in "dry" applications such as a facial or bath tissue, contain anionic particles. Examples of suitable anionic particles for use in the cleansing formulations of the present invention include anionic polymers, inorganic anionic species, and biological anionic polymers. Suitable anionic particles and/or microfibers can be selected from the group consisting of polyglutamic acid, albumin, heparin, alginic acid, polyaspartic acid, polyacrylic acid, polyamino acid, allophane, kaolinite, halloysite, montmorillonite, illite, chlorite, vermiculite, sepiolite, attapulgite, palygorskite, benonite, laponite, silicate, aluminosilicate, titanium dioxide, aluminum, cellulose carbonate, oxycellulose, carboxymethyl chitin, carboxymethyl chitosan, carboxymethyl curdlan, carboxymethyl alpha-cyclodextrin, carboxymethyl beta-cyclodextrin, carboxymethyl dextran, carboxymethyl guaran, dextran hexanioc acid, dextran polyaldehyde, guar polyaldehyde type I, guar polyaldehyde type II, carboxymethyl konjac, guar polycarboxylic acid, locust bean gum polyalkehyde type I, carboxymethyl locust bean gum, carboxymethyl canthan, carboxymethylcellulose cellulose, cellulose phosphate, sulfoxythyl cellulose, derivitized organic and inorganic particles, anionic derivatives of carbohydrates, and mixtures and combinations thereof. Carboxymethylcellulose microfibers are a preferred anionic material for use in the present invention.

The anionic particles, microfibers, or compounds useful in the cleansing formulations of the present invention typically have a diameter of from about 0.1 micrometers to about 10 micrometers, preferably from about 1 micrometer to about 8 micrometers, more preferably from about 2 micrometers to about 6 micrometers, and most preferably from about 3 micrometers to about 4 micrometers. If the anionic particle utilized in the charge-modified formulations of the present invention is a microfiber, such as a carboxymethylcellulose microfiber, typically the fiber will have a length of less than about 1 millimeter, preferably less than about 0.5 millimeters, and still more preferably less than about 0.3 millimeters. It has been discovered that an especially preferred microfiber for use in the cleansing formulations of the present invention is a carboxymethylcellulose microfiber having diameter of from about 3 to about 4 micrometers and a length of less than about 10 micrometers.

The anionic particles are present in the charge-modified formulations of the present invention in an amount effective to result in improved cleaning properties of the solution through electrostatic interactions with contaminants and the skin. Typically, the anionic particles are present in the formulation in an amount from about 0.001 mg/(mL of cleansing solution) to about 10 mg/(mL of cleansing solution), preferably from about 0.01 mg/(mL of cleansing solution) to about 0.5 mg/(mL of cleansing solution), and still more preferably from about 0.01 mg/(mL of cleansing solution) to about 0.25 mg/(mL of cleansing solution), and still more preferably from about 0.01 mg/(mL of cleansing solution) to about 0.1 mg/(mL of cleansing solution.) If the anionic particles are to be incorporated into a non-hydrated product such as a tampon, facial tissue, bath tissue, or wound dressing, for example, the particles are typically present in an amount from about 0.001 mg/(g of substrate) to about 10 mg/(g of substrate), preferably from about 0.01 mg/(g of substrate) to about 5 mg/(g of substrate), and still more preferably from about 0.01 mg/(g of substrate) to about 0.25 mg/(g of substrate), and still more preferably from about 0.01 mg/(g of substrate) to about 0.1 mg/(g of substrate.) The exact amount of anionic particles required for incorporation into the cleansing products of the present invention will depend on numerous factors such as the initial net charge of the contaminant, the net charge of the anionic particles, and the net charge required to displace the contaminant from the skin. A significant advantage of the present invention is that only a small amount of anionic particle or microfiber is required to significantly increase the ability of a cleansing formulation to remove contaminants from skin. Another significant advantage of the present invention is that when used in combination with a substrate, once the anionic particles have dislodged the contaminant from the skin surface, the contaminant can easily be bound to the substrate and removed from the skin.

The anionic particles and/or microfibers for incorporation into the cleansing formulations of the present invention have a net anionic charge, and may sometimes be referred to as cation exchangers. Typically, the cleansing formulations of the present invention contain anionic particles and/or microfibers having sufficient negative charge to impart improved cleaning characteristics into the formulations through electrostatic interactions with contaminants and skin. The amount of anionic charge on a particular particle or microfiber can vary substantially and can be measured utilizing several different units. Cationic exchangers are sometimes referred to as having a "capacity" which may be measured in microequivalents per gram or milliequivalents per gram, or may be measured in terms of the amount of a certain protein that the cation exchanger will bind. For example, the capacity of a cation exchanger may be given in terms of the number of grams of albumin that one gram of cation exchanger will bind; i.e. certain carboxymethylcellulose fibers have an exchange capacity of about 100 nanograms albumin per milligram of carboxymethylcellulose fibers. Still another way of referring to the amount of anionic charge is in terms of micro or milli-equivalents per unit area. One skilled in the art will recognize that the exchange capacity units or negativity units can be converted from one form to another to calculate proper amounts of charge density for use in the present invention.

Typically, the anionic particles and/or microfibers present in charge-modified formulations of the present invention have an effective charge density of from about 0.1 microequivalents/g to about 500 milliequivalents/g or more. Although effective charge densities of more than about 500 milliequivalents/g can be used in the cleansing formulations of the present invention, such a large charge density is not typically required to realize the benefit of the present invention. In some embodiments of the present invention, the anionic particles and/or microfibers preferably have an effective charge density of from about 0.1 microequivalents/g to about 1000 microequivalents/g, more preferably from about 0.1 microequivalents/g to about 100 microequivalents/g, and still more preferably from about 0.1 microequivalents/g to about 10 microequivalents/g.

If the anionic particles and/or microfibers are to be incorporated into a liquid cleansing solution useful, for example, with a fibrous wet wipe substrate, typically the cleansing solution will have a pH of from about 2 to about 9, more preferably from about 4 to about 7, and still more preferably from about 5 to about 6. Although the anionic particle-containing formulations of the present invention are active over a wide range of pH values, the above-referenced ranges provide optimum performance.

In one embodiment, the charge-modified formulations of the present invention can be incorporated into a cleansing cloth, pre-moistened wipe, wet wipe, udder wipe, hand wipe, face wipe, cosmetic wipe, household wipe, hospital wipe, industrial wipe and the like having improved contaminant removing characteristics while being gentle to the skin. Materials suitable for the substrate of the wet wipe are well known to those skilled in the art, and are typically made from a fibrous sheet material which may be either woven or nonwoven. For example, the wet wipes incorporating the charge-modified formulations of the present invention may include nonwoven fibrous sheet materials which include meltblown, coform, air-laid, bonded-carded web materials, hydroentangled materials, and combinations thereof. Such materials can be comprised of synthetic or natural fibers, or a combination thereof. Typically, wet wipes define a basis weight of from about 25 to about 120 grams per square meter and desirably from about 40 to about 90 grams per square meter.

In a particular embodiment, the wet wipes incorporating the charge-modified formulations of the present invention comprise a coform basesheet of polymeric microfibers and cellulosic fibers having a basis weight of from about 60 to about 80 grams per square meter and desirably about 75 grams per square meter. Such coform basesheets are manufactured generally as described in U.S. Pat. No. 4,100,324, which is incorporated by reference. Typically, such coform basesheets comprise a gas-formed matrix of thermoplastic polymeric meltblown microfibers, such as, for example, polypropylene microfibers, and cellulosic fibers, such as, for example, wood pulp fibers.

The relative percentages of the polymeric microfibers and cellulosic fibers in the coform basesheet can vary over a wide range depending upon the desired characteristics of the wet wipes. For example, the coform basesheet may comprise from about 20 to about 100 weight percent, desirably from about 20 to about 60 weight percent, and more desirably from about 30 to about 40 weight percent of the polymeric microfibers based on the dry weight of the coform basesheet being used to provide the wet wipes.

Alternatively, the wet wipes incorporating the charge-modified formulations of the present invention can comprise a composite which includes multiple layers of materials. For example, the wet wipes may include a three-layer composite which includes an elastomeric film or meltblown layer between two coform layers as described above. In such a configuration, the coform layers may define a basis weight of from about 15 to about 30 grams per square meter and the elastomeric layer may include a film material such as a polyethylene metallocene film.

As previously mentioned, the wet wipes contain a cleansing formulation which is absorbed into the wet wipes. The amount of solution contained within each wet wipe may vary depending upon the type of material being used to provide the wet wipe, the type of solution being used, the type of container being used to store the wet wipes, and the desired end use of the wet wipes. Generally, each wet wipe can contain from about 150 to about 600 weight percent and desirably from about 250 to about 450 weight percent solution based on the dry weight of the wipe for improved wiping. In a particular aspect, wherein the wet wipes are made from a coform material comprising from about 30 to about 40 weight percent polymeric microfibers based on the dry weight of the wipe, the amount of solution contained within the wet wipe is from about 300 to about 400 weight percent and desirably about 330 weight percent based on the dry weight of the wet wipe. If the amount of solution is less than the above-identified range, the wet wipe may be too dry and may not adequately perform. If the amount of solution is greater than the above-identified range, the wet wipe may be oversaturated and soggy and the solution may pool in the bottom of the container holding the wet wipes.

The charge-modified cleansing solutions of the present invention which can be incorporated into wet wipes may also optionally contain a variety of other components which may assist in providing the desired wiping and cleaning properties. For example, additional components may include water, emollients, surfactants, preservatives, chelating agents, pH buffers, fragrances, antimicrobial actives, acids, alcohols, or combinations or mixtures thereof. The solution may also contain lotions and/or medicaments to deliver any number of cosmetic and/or drug ingredients to improve performance. To provide reduced skin irritation, the solution desirably includes at least about 80 weight percent water and more desirably at least about 90 percent water based on the total weight of the solution.

In another embodiment, the charge-modified formulations of the present invention incorporating anionic particles, compounds, or microfibers can be incorporated into a substrate which can be a woven web, non-woven web, spunbonded fabric, meltblown fabric, knit fabric, wet laid fabric, needle punched web, cellulosic material or web, and combinations thereof, for example, to create products such as facial tissue, bathroom tissue, diapers, training pants, incontinence garments, nursing pads, feminine care products such as tampons and sanitary napkins, hand towels, surgical drapes, wound dressings, gowns, bedsheets, pillowcases, body cleansing cloths, mouthrinse, hand mitts, vaginal wipe, douche, oral mouth swab, finger mitts, dry acne wipes, oil blotting paper and the like. Many of these products are utilized to absorb liquids such as urine, feces, menses, and blood which may contain potentially harmful or aesthetically undesirable contaminants.

The addition of the charge-modified solution to the substrate may be performed using a liquid application treater such as a DAHLGREN® LAS. This application system applies a wet solution comprising the anionic particles, compounds or microfibers to the substrate followed by a drying process to produce a dry substrate containing the anionic particles, compounds, or microfibers. This system is commercially available and well known to those skilled in the art.

In another embodiment, the charge-modified solution comprising the anionic particles, compounds, or microfibers can be added to a substrate through spray coating, slot coating and printing, or a combination thereof. With spray coating, the anionic particles are first thoroughly mixed with a soluble adhesive agent to disperse the anionic particles throughout the adhesive material. The adhesive material utilized should be substantially soluble in mucus, feces, urine, or water, depending upon the intended application of the resulting product. Further, the adhesive material should be substantially non-reactive with the anionic particles and should not substantially alter the electrical properties and charges of the particles.

The adhesive material can comprise a soluble adhesive which will partially or completely dissolve upon use of the resulting product in a hydrous environment. Suitable soluble adhesives may include, for example, polyvinyl pyrrolidone and polyvinyl alcohol, and combinations thereof. After the adhesive and anionic particles are thoroughly mixed, they can be applied onto the desired area of the product of the present invention by spray coating, knifing, or roller coating, for example, and allowed to dry prior to use.

Similar to spray coating, the anionic particles may be introduced onto substrates through slot coating. In slot coating, an adhesive-anionic particle mixture as discussed above is introduced directly onto the desired area of the pad in "slots" or discrete row patterns.

In an alternative embodiment, the anionic particles can also be introduced onto a substrate through the use of a vacuum driving force. The anionic particles are positioned on the substrate while a vacuum driving force is applied to the opposite side of the substrate to drive the anionic particles into the fabric matrix substrate.

As mentioned above, it is preferred that the cleansing compositions of the present invention be utilized in a hydrated environment for maximum effectiveness. When the aforementioned dry products contact feces or menses, for example, on the skin, the environment becomes sufficiently hydrous for the cleansing solution to be highly effective.

The following examples, which are merely for the purpose of illustration and are not to be regarded as limiting the scope of the invention or manner in which it may be practiced, illustrate the present invention.

EXAMPLE 1

In this Example, various anionic particle formulations were tested to determine their effectiveness in dislodging *Candida albicans* from human skin.

*Candida albicans* (ATCC 10231) was obtained from the American Type Culture Collection (ATCC) (Rockville, Md.) and was cultured onto a Sabourands medium fortified with glucose (SAB-Dex) agar plate (Becton Dickinson, Cockeysville, Md.) overnight at 37° C. The following day, 2–3 isolated *Candida albicans* colonies were inoculated into SAB-Dex Broth (20 mL) and incubated for 18 hours at 32° C. while shaking at 220 rpm. The resulting broth culture was diluted to $1 \times 10^5$ CFU/mL with phosphate buffer (pH=7.2) (VWR Industries, Batavia Ill., Catalogue Number 16161-601).

The release of *Candida albicans* from skin tape strips was measured utilizing the following procedure. Skin tape strips were first made by pulling D-Squame skin sampling discs (CuDerm Corporation, Dallas, Tex.) four times from adjacent adult male volar forearm sites. The skin tape strips were then placed into deep six-well plates (Becton Dickinson, Franklin Lakes, N.J.) and blocked with 2.0 mL of 5% Bovine Serum Albumin (BSA) (Sigma, St. Louis, Mo.) in Phosphate Buffer Solution (150 mM NaCl, 50 mM Potassium Phosphate at a pH=7.4) for 60 minutes at 33° C. while shaking at 220 rpm.

After the shaking was discontinued, the fluid in each well was removed and *Candida albicans* (1 mL, about 1×10⁵ CFU/mL) was added to each tape strip, followed by the addition of Trypticase Soy Broth (Difco Labs, Detroit, Mich.) (1 mL) to each tape strip, and the plates incubated at 33° C. for about 60 minutes. After incubation, the fluid was aspirated, and the tape strips were washed three times with Tris-Buffered Saline (50 mM Tris (base), 150 mM Sodium Chloride, at pH=7.4) (3.0 mL). After washing both sides of the tape strips with Tris-Buffered Saline, the skin tape strips were placed in a fresh, clean 6-well plate.

The materials, along with the use concentration, exchange capacity, and sizes used in the test formulations are listed in Table 1. A suspension of each test material listed in Table 1 in Tris-Buffered Saline (2 mL) was placed on top of the tape strips. Along with each test formulation, a corresponding control was run which did not include any test material. With each control, only Tris-Buffered Saline was placed on top of the tape strips. The strips were incubated for 60 minutes at room temperature while shaking at 220 rpm, and then were washed with water three times. Each tape strip was then fixed by adding 2.5% Glutaraldehyde (Sigma Chemical, St. Louis, Mo.) (2.0 mL) to each of the wells and allowing the mixture to stand for ten minutes. After standing for ten minutes, the tape strips were washed three times with distilled water (3.0 mL) and stained by adding 0.5 mL Calcofluor White (Difco, Ann Arbor, Mich., Catalogue Number 3571-26-3) to each well and allowing the mixture to stand for about 15 minutes. After standing, the tape strips were again washed three times with distilled water and allowed to air dry. Each test formulation and control were prepared in triplicate.

TABLE 1

| Material | Use Concentration | Exchange Capacity | Size Diameter | Supplier |
| --- | --- | --- | --- | --- |
| CM-Cellulose | 0.4 mg/mL | 3 microequivalents/g | 3–4 micron | SCIGEN |
| PEI-Cellulose | 0.4 mg/mL | 1 microequivalent/g | 3–4 micron | SCIGEN |
| DEAE-Cellulose | 0.4 mg/mL | 1 microequivalent/g | 3–4 micron | SCIGEN |
| Bentonite | 8.0 mg/mL | No Charge | Powder | Sigma |
| CM-Cellulose | 8.0 mg/mL | 3 microeqivalents/g | Fibrous | Sigma |
| Cellulose | 8.0 mg/mL | No Charge | Fibrous | Sigma |
| DEAE-Cellulose | 8.0 mg/mL | 1 millieqivalent/g | Fibrous | Sigma |
| QAE-Cellulose | 8.0 mg/mL | 0.92 milliequivalents/g | Fibrous | Sigma |
| Cellulose Phosphate | 8.0 mg/mL | 3.8 milliequivalents/g | Powder | Sigma |
| Chitin | 8.0 mg/mL | No Charge | Powder | Sigma |

After drying, the yeast cells were enumerated visually with an Olympus BH2 fluorescent microscope fitted with a 405 nm excitation filter and a 455 nm barrier filter. The counting procedure included placing the tape strips with the crescent label near the bottom edge onto a microscope slide perpendicular to the microscope objective. A 20× objective was utilized to dissect the field of view of the tape strip in the middle. Only the yeast cells in this middle field of view (approximately $2 \times 10^7$ $\mu m^2$) were counted. The field of view was about 5% of the total tape strip. The percent removal of *Candida albicans* was calculated as follows:

[(# of Control Cells−# of Sample Cells)/# of Control Cells]×100

Typically, approximately 5,000–10,000 yeast cells were bound to a 22 mm diameter D-Squame tape strip under the experimental conditions. The results are shown in Table 2.

TABLE 2

| Material | Use Concentration | Control Count (Ave) | Test Count (Ave) | % Removal |
| --- | --- | --- | --- | --- |
| CM-Cellulose | 0.4 mg/mL | 173 | 4 | 97.7 |
| PEI-Cellulose | 0.4 mg/mL | 171 | 109 | 36.6 |
| DEAE-Cellulose | 0.4 mg/mL | 172 | 147 | 14.5 |
| Bentonite | 8.0 mg/mL | 321 | 198.7 | 38.2 |
| CM-Cellulose | 8.0 mg/mL | 321 | 317 | 1.5 |
| Cellulose | 8.0 mg/mL | 321 | 294.7 | 8.4 |
| DEAE-Cellulose | 8.0 mg/mL | 321 | 293.3 | 8.8 |
| QAE-Cellulose | 8.0 mg/mL | 322 | 289 | 10.2 |
| Cellulose Phosphate | 8.0 mg/mL | 322 | 339.3 | N/A |
| Chitin | 8.0 mg/mL | 322 | 279.7 | 13.1 |

As Table 2 indicates, about 98% of the *Candida albicans* cells were released from the skin tape by the carboxymethylcellulose anionic fibers having a diameter of from about 3 to about 4 micrometers.

EXAMPLE 2

In this Example, carboxymethylcellulose fibers having a diameter of about 3–4 micrometers and a cationic exchange capacity of about 3 microequivalents/g were exposed to skin tape containing *Candida albicans* and the ability of the carboxymethylcellulose fibers to release the *Candida albicans* from the skin was measured.

*Candida albicans* (ATCC 10231) was obtained from the American Type Culture Collection (ATCC) (Rockville, Md.) and was cultured prior to experimentation onto a Sabourands medium fortified with glucose (SAB-Dex) agar plate (Becton Dickinson, Cockeysville, Md.) overnight at 37° C. The following day, 2–3 isolated *Candida albicans* colonies were inoculated into SAB-Dex Broth (20 mL) and incubated for 18 hours at 32° C. while shaking at 220 rpm. The resulting broth culture was diluted to 1×10⁵ CFU/mL with phosphate buffer (pH=7.2) (VWR Industries, Batavia Ill.).

Skin tape strips were first made by pulling D-Squame skin sampling discs (CuDerm Corporation, Dallas, Tex.) four times from adjacent adult male volar forearm sites. The skin tape strips were then placed into deep six-well plates (Becton Dickinson, Franklin Lakes, N.J.) and blocked with 2.0 mL of 5% Bovine Serum Albumin (BSA) (Sigma, St. Louis, Mo.) in Phosphate Buffer Solution (150 mM NaCl, 50 mM Potassium Phosphate at a pH=7.4) for 60 minutes at 33° C. while shaking at 220 rpm.

Figure 1:
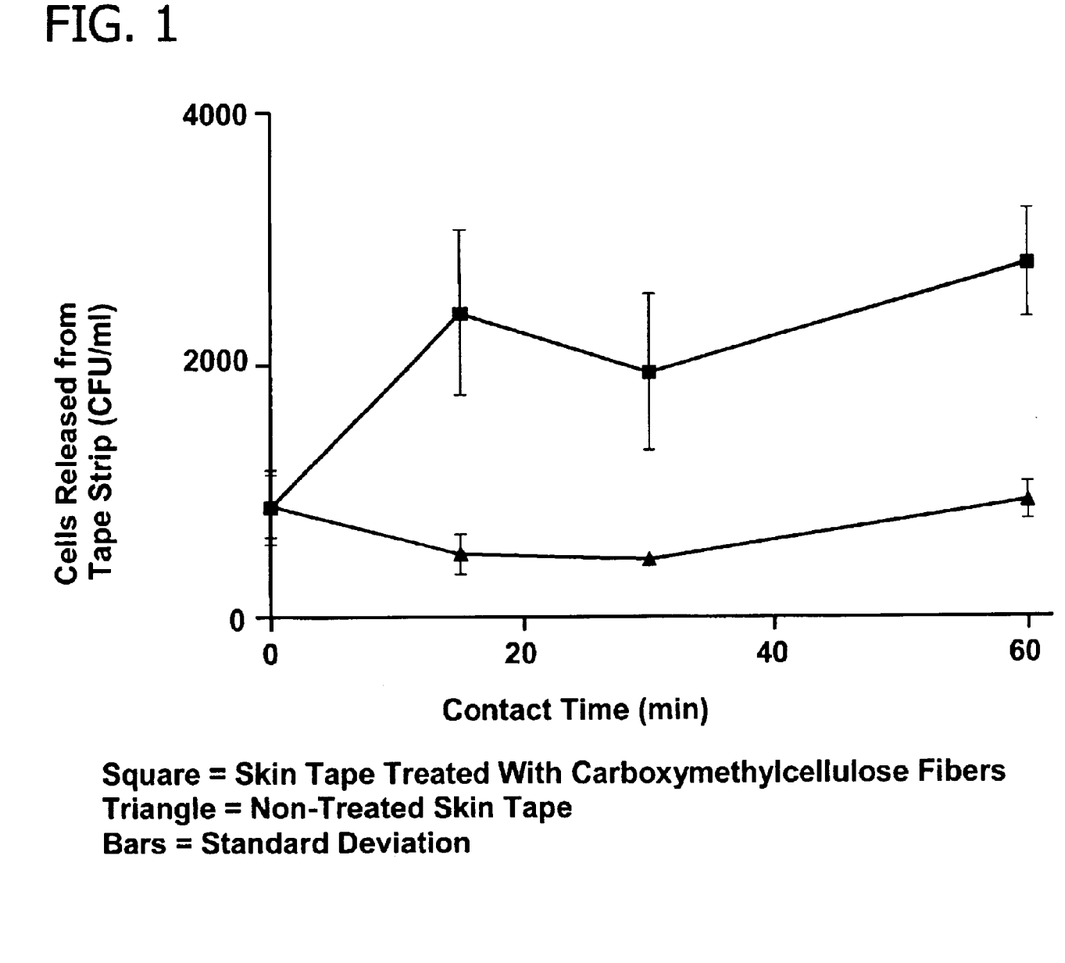
FIG. 1 is a graph showing the relationship between time and the number of *Candida albicans* cells released from a skin tape strip upon exposure to carboxymethylcellulose fibers.

After shaking, a suspension of carboxymethylcellulose (3–4 micrometer diameter, cationic exchange capacity of about 3 microequivalents/g) (2.0 mL of 0.25 mg/mL) in Tris Buffered Saline was placed on top of the skin tape strips. An equal amount of Tris-Buffered Saline was added to the control. The skin tape strips were incubated for 60 minutes at room temperature while shaking at 220 rpm. Prior to the addition of the carboxymethylcellulose fibers and at time intervals of 15, 30, and 60 minutes samples of fluid from above the skin tape strips (in triplicate) were collected and plated on Sabourads agar and the viable number of yeast cells in solution determined by incubating for 24 hours at 33° C. and counting the yeast colonies. The results are shown in FIG. 1. Further, just prior to the introduction of the carboxymethylcellulose fibers and after 20 minutes photomicrographs of the skin tape were taken. These photomicrographs are shown in FIGS. 2 and 3 where *Candida*

*albicans* appears as bluish-white rods. These photomicrographs were taken with an Olympus BH2, UV excitation and a SPOT digital camera.

As FIG. 1 indicates, the carboxymethylcellulose fibers utilized in this Example were highly successful in removing yeast cells from the skin tape strips. Just prior to the addition of the carboxymethylcellulose fibers, approximately 1000 yeast cells were present in the solution. After only about 15 minutes, the carboxymethylcellulose fibers had removed about 1200 more yeast cells from the skin tape, while the control showed virtually no change.

Figure 2:
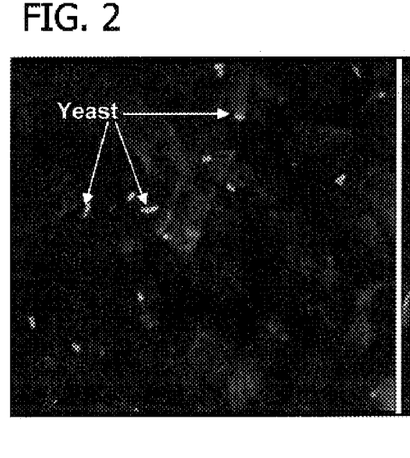
FIG. 2 is a photomicrograph of a skin tape strip containing *Candida albicans* cells prior to exposure of the skin tape strip to carboxymethylcellulose fibers.
Figure 3:
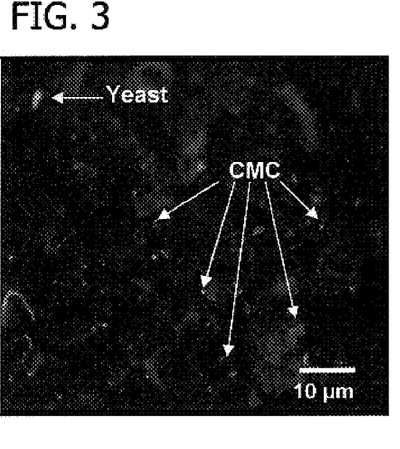
FIG. 3 is a photomicrograph of a skin tape strip showing both *Candida albicans* cells and carboxymethylcellulose fibers after a skin tape strip has been exposed to carboxymethylcellulose fibers.

Referring now to FIG. 2, there is shown a photomicrograph of the skin tape prior to it being subjected to the carboxymethylcellulose fibers. Numerous yeast cells, shown as bluish-white rods, are easily seen on the surface of the skin tape. Referring now to FIG. 3, there is shown a photomicrograph of the same skin tape after being subjected to the carboxymethylcellulose fibers described above for 20 minutes. It is easily seen that a significant amount of the yeast cells have been dislodged from the tape demonstrating the carboxymethylcellulose's ability to dislodge yeast cells.

EXAMPLE 3

In this Example, carboxymethylcellulose fibers having a diameter of about 3–4 micrometers and a cationic exchange capacity of about 3 microequivalents/g were introduced into various buffers having a range of pHs to determine the pH range over which carboxymethylcellulose fibers can remove *Candida albicans* from the skin.

*Candida albicans* (ATCC 10231) was obtained from the American Type Culture Collection (ATCC) (Rockville, Md.) and was cultured prior to experimentation onto a Sabourands medium fortified with glucose (SAB-Dex) agar plate (Becton Dickinson, Cockeysville, Md.) overnight at 37° C. The following day, 2–3 isolated *Candida albicans* colonies were inoculated into SAB-Dex Broth (20 mL) and incubated for 18 hours at 32° C. while shaking at 220 rpm. The resulting broth culture was diluted to $1 \times 10_5$ CFU/mL with phosphate buffer (pH=7.2) (VWR Industries, Batavia Ill.).

Skin tape strips were first made by pulling D-Squame skin sampling discs (CuDerm Corporation, Dallas, Tex.) four times from adjacent adult male volar forearm sites. The skin tape strips were then placed into deep six-well plates (Becton Dickinson, Franklin Lakes, N.J.) and blocked with 2.0 mL of 5% Bovine Serum Albumin (BSA) (Sigma, St. Louis, Mo.) in Phosphate Buffer Solution (150 mM NaCl, 50 mM Potassium Phosphate at a pH=7.4) for 60 minutes at 33° C. while shaking at 220 rpm.

After shaking, the fluid was removed from each well and *Candida albicans* (1.0 mL of $10^5$ CFU/mL) and Trypticase Soy Broth (Difco Labs, Detroit, Mich.) (1.0 mL) was added to each skin tape strip, and the plates were incubated at 33° C. for 60 minutes. The fluid was aspirated and the skin tape strips were removed and washed three times with 3.0 mL of Tris-Buffered Saline (50 mM Tris (base), 150 mM Sodium Chloride at a pH=7.4).

For testing, the following test suspensions were prepared: Carboxymethylcellulose (2.0 mL of 0.25 mg/mL 3–4 micrometer fibers having a cationic exchange capacity of about 100 ng albumin/mg) was added to the following buffer solutions: Citrate Phosphate (0.1 M) at a pH of (1) 4.2; (2) 5.2; and (3) 6.2; TRIS (0.1M) at a pH of (1) 7.2; and (2) 8.2; HEPES (50 mM) at a pH of (1) 6.2; (2) 7.2; and (3) 8.2; and Phosphate (50 mM) at a pH of (1) 6.2; (2) 7.2; and (3) 8.2. After preparation, the 2 mL suspension containing the carboxymethylcellulose and each buffer was added to a separate well in the plate. The skin tape strips were then incubated for 60 minutes at room temperature while shaking at 220 rpm. After shaking, the skin tape strips were washed three times with water, and fixed by adding 2.0 mL of 2.5% Glutaraldehyde to each of the wells of the plate for 10 minutes. After the 10 minutes, the skin tape strips were washed three times with distilled water, and stained by adding 0.5 mL Calcofluor White (Difco, Ann Arbor, Mich.) to the well for about 15 minutes. Then, the skin tape strips were washed 3 times with distilled water and allowed to air dry. After air-drying, the yeast cells were enumerated and percent removal was calculated as described above.

Figure 4:
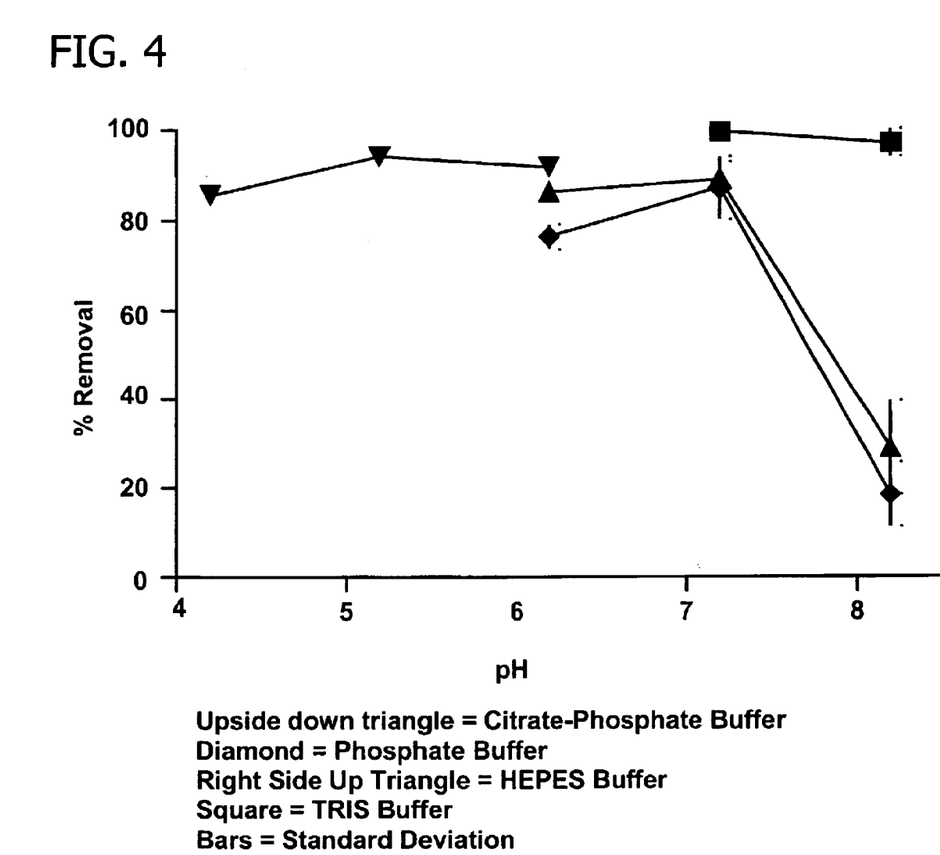
FIG. 4 is a graph showing the relationship of the pH of solutions containing carboxymethylcellulose fibers and percent *Candida albicans* removed from a skin tape strip.

The results of this Example are shown in FIG. 4. As shown in FIG. 4, the carboxymethylcellulose was able to displace the yeast from the skin tape over a wide range of pH values. With various buffer solutions, the yeast particles had a greater than 70% removal rate at pH values up to about 8.2.

EXAMPLE 4

In this Example, carboxymethylcellulose fibers were tested to determine whether the fibers acted as an antimicrobial agents.

*Candida albicans* (ATCC 10231) was obtained from the American Type Culture Collection (ATCC) (Rockville, Md.) and was cultured prior to experimentation onto a Sabourands medium fortified with glucose (SAB-Dex) agar plate (Becton Dickinson, Cockeysville, Md.) overnight at 37° C. The following day, 2–3 isolated *Candida albicans* colonies were inoculated into SAB-Dex Broth (20 mL) and incubated for 18 hours at 32° C. while shaking at 220 rpm. The resulting broth culture was diluted to $1 \times 10^5$ CFU/mL with phosphate buffer (pH=7.2) (VWR Industries, Batavia Ill.).

*Candida albicans* (2.0 mL of $1 \times 10^5$ CFU/mL) was mixed with 2 mL of phosphate buffer solution (150 mM Sodium Chloride, 50 mM Potassium Phosphate, at pH=7.4) and incubated with 2.0 mL of Tris-Buffered Saline and carboxymethylcellulose fibers (3–4 micrometer diameter, 0.5 mg/mL and a cation exchange capacity of about 3 microequivalents/g). A second test sample was prepared comprising *Candida albicans* (2.0 mL of $1 \times 10^5$ CFU/mL) mixed with 2 mL of phosphate buffer solution and 2.0 mL of Tris-Buffered Saline and cellulose phosphate fibers (3–4 micrometer diameter, 0.5 mg/mL and an effective charge density of 3.8 milliequivalents/g). Also, a control was prepared without any cellulose material.

The test solutions were incubated for 210 minutes at 33° C., with samples being taken prior to incubation, and after 15, 30, 60 and 210 minutes. The samples were evaluated for the number of viable cells. Table 3 shows the viability of *Candida albicans* at various times during incubation after exposure to carboxymethylcellulose and cellulose. As the results indicate, neither the carboxymethylcellulose nor the cellulose phosphate had any significant effect on yeast viability.

TABLE 4

| Exposure | CFU/mL | | |
|---|---|---|---|
| Time (min) | Control | CMC | Cellulose Phosphate |
| 0 | $1.12 \times 10^5$ | $1.07 \times 10^5$ | $1.12 \times 10^5$ |
| 15 | $1.29 \times 10^5$ | $1.27 \times 10^5$ | $1.35 \times 10^5$ |
| 30 | $1.31 \times 10^5$ | $1.14 \times 10^5$ | $1.18 \times 10^5$ |

TABLE 4-continued

| Exposure Time (min) | CFU/mL | | |
|---|---|---|---|
| | Control | CMC | Cellulose Phosphate |
| 60 | $1.27 \times 10^5$ | $1.29 \times 10^5$ | $1.66 \times 10^5$ |
| 210 | $8.45 \times 10^4$ | $9.97 \times 10^4$ | $1.35 \times 10^5$ |

In view of the above, it will be seen that the several objects of the invention are achieved. As various changes could be made in the above-described cleansing formulations without departing from the scope of the invention, it is intended that all matter contained in the above description be interpreted as illustrative and not in a limiting sense.

What is claimed is:

1. A wet wipe comprising a fibrous sheet material and a cleansing solution capable of dislodging contaminants from skin, the cleansing solution comprising from about 0.001 mg/(mL of cleansing solution) to about 10 mg/(mL of cleansing solution) of anionic particles having a diameter of from about 0.1 micrometers to about 10 micrometers, the anionic particles having an effective charge density of from about 0.1 microequivalents/g to about 500 milliequivalents/g, wherein the anionic particles are selected from the group consisting of cellulose carbonate, carboxymethyl chitin, carboxymethyl chitosan, carboxymethyl curdlan, carboxymethyl alpha-cyclodextrin, carboxymethyl beta-cyclodextrin, carboxymethyl dextran, and carboxymethylcellulose.

2. The wet wipe as set forth in claim 1 wherein the cleansing solution comprises from about 0.01 mg/(mL of cleansing solution) to about 5 mg/(mL of cleansing solution) of the anionic particles.

3. The wet wipe as set forth in claim 1 wherein the cleansing solution comprises from about 0.01 mg/(mL of cleansing solution) to about 0.25 mg/(mL of cleansing solution) of the anionic particles.

4. The wet wipe as set forth in claim 1. wherein the cleansing solution comprises from about 0.01 mg/(mL of cleansing solution) to about 0.1 mg/(mL of cleansing solution) of the anionic particles.

5. The wet wipe as set forth in claim 1 wherein the effective charge density of the anionic particles is from about 0.1 microequivalents/g to about 1000 microequivalents/g.

6. The wet wipe as set forth in claim 1 wherein the effective charge density of the anionic particles is from about 0.1 microequivalents/g to about 100 microequivalents/g.

7. The wet wipe as set forth in claim 1 wherein the effective charge density of the anionic particles is from about 0.1 microequivalents/g to about 10 microequivalents/g.

8. The wet wipe as set forth in claim 1 wherein the diameter of the anionic particles is from about 1 micrometer to about 8 micrometers.

9. The wet wipe as set forth in claim 1 wherein the diameter of the anionic particles is from about 2 micrometers to about 6 micrometers.

10. The wet wipe as set forth in claim 1 wherein the diameter of the anionic particles is from about 3 micrometers to about 4 micrometers.

11. A wet wipe comprising a fibrous sheet material and a cleansing solution capable of dislodging contaminants from skin, the cleansing solution comprising from about 0.001 mg/(mL of cleaning solution) to about 10 mg/(mL of cleansing solution) of anionic particles having a diameter of from about 0.1 micrometers to about 10 micrometers, the anionic particles having an effective charge density of from about 0.1 microequivalents/g to about 500 milliequivalents/g, wherein the anionic particles are carboxymethylcellulose microfibers.

12. The wet wipe as set forth in claim 11 wherein the carboxymethylcellulose microfibers have a diameter of from about 2 micrometers to about 6 micrometers.

13. The wet wipe as set forth in claim 11 wherein the carboxymethylcellulose microfibers have a diameter of from about 3 micrometers to about 4 micrometers.

14. The wet wipe as set forth in claim 11 wherein the solution comprises from about 0.25 mg/(mL of the cleansing solution) to about 1 mg/(mL of the cleansing solution) of the carboxymethylcellulose microfibers.

15. The wet wipe as set forth in claim 11 wherein the carboxymethylcellulose fibers have an effective charge density of about 3 microequivalents/g.

16. A wet wipe comprising a fibrous sheet material and a cleansing solution capable of dislodging contaminants from skin, the cleansing solution having a pH of from about 5 to about 6 and comprising from about 0.001 mg/(mL of cleansing solution) to about 10 mg/(mL of cleansing solution) of anionic particles having a diameter of from about 0.1 micrometers to about 10 micrometers, the anionic particles having an effective charge density of from about 0.1 microequivalents/g to about 500 milliequivalents/g, wherein the anionic particles are selected from the group consisting of cellulose carbonate, carboxymethyl chitin, carboxymethyl chitosan, carboxymethyl curdlan, carboxymethyl alpha-cyclodextrin, carboxymethyl beta-cyclodextrin, carboxymethyl dextran, and carboxymethylcellulose.

17. The wet wipe as set forth in claim 16 wherein the cleansing solution comprises from about 0.01 mg/(mL of cleansing solution) to about 5 mg/(mL of cleansing solution) of the anionic particles.

18. The wet wipe as set forth in claim 16 wherein the cleansing solution comprises from about 0.01 mg/(mL of cleansing solution) to about 0.25 mg/(mL of cleansing solution) of the anionic particles.

19. The wet wipe as set forth in claim 16 wherein the cleansing solution comprises from about 0.01 mg/(mL of cleansing solution) to about 0.1 mg/(mL of cleansing solution) of the anionic particles.

20. The wet wipe as set forth in claim 16 wherein the effective charge density of the anionic particles is from about 0.1 microequivalents/g to about 1000 microequivalents/g.

21. The wet wipe as set forth in claim 16 wherein the effective charge density of the anionic particles is from about 0.1 microequivalents/g to about 100 microequivalents/g.

22. The wet wipe as set forth in claim 16 wherein the effective charge density of the anionic particles is from about 0.1 microequivalents/g to about 10 microequivalents/g.

23. The wet wipe as set forth in claim 16 wherein the diameter of the anionic particles is from about 1 micrometer to about 8 micrometers.

24. The wet wipe as set forth in claim 16 wherein the diameter of the anionic particles is from about 2 micrometers to about 6 micrometers.

25. The wet wipe as set forth in claim 16 wherein the diameter of the anionic particles is from about 3 micrometers to about 4 micrometers.

26. The wet wipe as set forth in claim 16 wherein the anionic particles are carboxymethylcellulose microfibers.

27. The wet wipe as set forth in claim 26 wherein the carboxymethylcellulose microfibers have a diameter of from about 2 micrometers to about 6 micrometers.

28. The wet wipe as set forth in claim 27 wherein the carboxymethylcellulose microfibers have a diameter of from about 3 micrometers to about 4 micrometers.

29. The wet wipe as set forth in claim 28 wherein the solution comprises from about 0.25 mg/(mL of the cleansing solution) to about 1 mg/(mL of the cleansing solution) of the carboxymethylcellulose microfibers.

30. The wet wipe as set forth in claim 29 wherein the carboxymethylcellulose fibers have an effective charge density of about 3 microequivalents/g.

31. A cleansing solution suitable for direct application to skin capable of dislodging contaminants from skin, the solution comprising from about 0.001 mg/(mL of cleansing solution) to about 10 mg/(mL of cleansing solution) of anionic particles having a diameter of from about 0.1 micrometers to about 10 micrometers, the anionic particles having an effective charge density of from about 0.1 microequivalents/g to about 500 milliequivalents/g, wherein the anionic particles are selected from the group consisting of cellulose carbonate, carboxymethyl chitin, carboxymethyl chitosan, carboxymethyl curdlan, carboxymethyl alpha-cyclodextrin, carboxymethyl beta-cyclodextrin, carboxymethyl dextran, and carboxymethylcellulose.

32. The cleansing solution as set forth in claim 31 wherein the cleansing solution comprises from about 0.01 mg/(mL of cleansing solution) to about 5 mg/(mL of cleansing solution) of the anionic particles.

33. The cleansing solution as set forth in claim 31 wherein the cleansing solution comprises from about 0.01 mg/(mL of cleansing solution) to about 0.25 mg/(mL of cleansing solution) of the anionic particles.

34. The cleansing solution as set forth in claim 31 wherein the cleansing solution comprises from about 0.01 mg/(mL of cleansing solution) to about 0.1 mg/(mL of cleansing solution) of the anionic particles.

35. The cleansing solution as set forth in claim 31 wherein the effective charge density of the anionic particles is from about 0.1 microequivalents/g to about 1000 microequivalents/g.

36. The cleansing solution as set forth in claim 31 wherein the effective charge density of the anionic particles is from about 0.1 microequivalents/g to about 100 microequivalents/g.

37. The cleansing solution as set forth in claim 31 wherein the effective charge density of the anionic particles is from about 0.1 microequivalents/g to about 10 microequivalents/g.

38. The cleansing solution as set forth in claim 31 wherein the diameter of the anionic particles is from about 1 micrometer to about 8 micrometers.

39. The cleansing solution as set forth in claim 31 wherein the diameter of the anionic particles is from about 2 micrometers to about 6 micrometers.

40. The cleansing solution as set forth in claim 31 wherein the diameter of the anionic particles is from about 3 micrometers to about 4 micrometers.

41. The cleansing solution as set forth in claim 31 wherein the anionic particles are carboxymethylcellulose microfibers.

42. The cleansing solution as set forth in claim 41 wherein the carboxymethylcellulose microfibers have a diameter of from about 2 micrometers to about 6 micrometers.

43. The cleansing solution as set forth in claim 42 wherein the carboxymethylcellulose microfibers have a diameter of from about 3 micrometers to about 4 micrometers.

44. The cleansing solution as set forth in claim 42 wherein the solution comprises from about 0.25 mg/(mL of the cleansing solution) to about 1 mg/(mL of the cleansing solution) of the carboxymethylcellulose microfibers.

45. The cleansing solution set forth in claim 44 wherein the carboxymethylcellulose fibers have an effective charge density of about 3 microequivalents/g.

46. A cleansing solution suitable for direct application to skin capable of dislodging contaminants from skin, the solution having a pH of from about 5 to about 6 and comprising from about 0.001 mg/(mL of cleansing solution) to about 10 mg/(mL of cleansing solution) of anionic particles having a diameter of from about 0.1 micrometers to about 10 micrometers, the anionic particles having an effective charge density of from about 0.1 microequivalents/g to about 500 milliequivalents/g, wherein the anionic particles are selected from the group consisting of cellulose carbonate, carboxymethyl chitin, carboxymethyl chitosan, carboxymethyl curdlan, carboxymethyl alpha-cyclodextrin, carboxymethyl beta-cyclodextrin, carboxymethyl dextran, and carboxymethylcellulose.

47. The cleansing solution as set forth in claim 46 wherein the cleansing solution comprises from about 0.01 mg/(mL of cleansing solution) to about 5 mg/(mL of cleansing solution) of the anionic particles.

48. The cleansing solution as set forth in claim 46 wherein the cleansing solution comprises from about 0.01 mg/(mL of cleansing solution) to about 0.25 mg/(mL of cleansing solution) of the anionic particles.

49. The cleansing solution as set forth in claim 46 wherein the cleansing solution comprises from about 0.01 mg/(mL of cleansing solution) to about 0.1 mg/(mL of cleansing solution) of the anionic particles.

50. The cleansing solution as set forth in claim 46 wherein the effective charge density of the anionic particles is from about 0.1 microequivalents/g to about 1000 microequivalents/g.

51. The cleansing solution as set forth in claim 46 wherein the effective charge density of the anionic particles is from about 0.1 microequivalents/g to about 100 microequivalents/g.

52. The cleansing solution as set forth in claim 46 wherein the effective charge density of the anionic particles is from about 0.1 microequivalents/g to about 10 microequivalents/g.

53. The cleansing solution as set forth in claim 46 wherein the diameter of the anionic particles is from about 1 micrometer to about 8 micrometers.

54. The cleansing solution as set forth in claim 46 wherein the diameter of the anionic particles is from about 2 micrometers to about 6 micrometers.

55. The cleansing solution as set forth in claim 46 wherein the diameter of the anionic particles is from about 3 micrometers to about 4 micrometers.

56. The cleansing solution as set forth in claim 46 wherein the anionic particles are carboxymethylcellulose microfibers.

57. The cleansing solution as set forth in claim 56 wherein the carboxymethylcellulose microfibers have a diameter of from about 2 micrometers to about 6 micrometers.

58. The cleansing solution as set forth in claim 57 wherein the carboxymethylcellulose microfibers have a diameter of from about 3 micrometers to about 4 micrometers.

59. The cleansing solution as set forth in claim 57 wherein the solution comprises from about 0.25 mg/(mL of the cleansing solution) to about 1 mg/(mL of the cleansing solution) of the carboxymethylcellulose microfibers.

60. The cleansing solution as set forth in claim 59 wherein the carboxymethylcellulose microfibers have an effective charge density of about 3 microequivalents/g.

61. A product comprising a substrate comprising anionic particles capable of dislodging contaminants from skin, the substrate comprising from about 0.001 mg/(g of substrate) to about 10 mg/(g of substrate) of anionic particles having a diameter of from about 0.1 micrometers to about 10 micrometers, the anionic particles having an effective charge density of from about 0.1 microequivalents/g to about 500 milliequivalents/g, wherein the anionic particles are selected from the group consisting of cellulose carbonate, carboxymethyl chitin, carboxymethyl chitosan, carboxymethyl curdlan, carboxymethyl alpha-cyclodextrin, carboxymethyl beta-cyclodextrin carboxymethyl dextran, and carboxymethylcellulose.

62. The product as set forth in claim 61 wherein the substrate comprises from about 0.01 mg/(g of substrate) to about 5 mg/(g of substrate) of the anionic particles.

63. The product as set forth in claim 61 wherein the substrate comprises from about 0.01 mg/(g of substrate) to about 0.25 mg/(g of substrate) of the anionic particles.

64. The product as set forth in claim 61 wherein the substrate comprises from about 0.01 mg/(g of substrate) to about 0.1 mg/(g of substrate) of the anionic particles.

65. The product as set forth in claim 61 wherein the effective charge density of the anionic particles is from about 0.1 microequivalents/g to about 1000 microequivalents/g.

66. The product as set forth in claim 61 wherein the effective charge density of the anionic particles is from about 0.1 microequivalents/g to about 3.00 microequivalents/g.

67. The product as set forth in claim 61 wherein the effective charge density of the anionic particles is from about 0.1 microequivalents/g to about 10 microequivalents/g.

68. The product as set forth in claim 61 wherein the diameter of the anionic particles is from about 1 micrometer to about 8 micrometers.

69. The product as set forth in claim 61 wherein the diameter of the anionic particles is from about 2 micrometers to about 6 micrometers.

70. The product as set forth in claim 61 wherein the diameter of the anionic particles is from about 3 micrometers to about 4 micrometers.

71. The product as set forth in claim 61 wherein the anionic particles are carboxymethylcellulose microfibers.

72. The product as set forth in claim 61 wherein the carboxymethylcellulose microfibers have a diameter of from about 2 micrometers to about 6 micrometers.

73. The product as set forth in claim 72 wherein the carboxymethylcellulose microfibers have a diameter of from about 3 micrometers to about 4 micrometers.

74. The product as set forth in claim 73 wherein the solution comprises from about 0.25 mg/(mL of the cleansing solution) to about 1 mg/(mL of the cleansing solution) of the carboxymethylcellulose microfibers.

75. The product as set forth in claim 61 wherein the substrate is selected from the group consisting of woven webs, non-woven webs, spunbonded fabrics, meltblown fabrics, wet-laid fabrics, needle punched webs, cellulosic material, or a combination thereof.

76. The product as set forth in claim 61 wherein the substrate is selected from the group consisting of facial tissue, bathroom tissue, diapers, training pants, incontinence garments, nursing pads, tampons, sanitary napkins, hand towels, surgical drapes, wound dressings, gowns, bedsheets, hand mitts, dry acne wipes, oil blotting paper and pillowcases.

* * * * *

UNITED STATES PATENT AND TRADEMARK OFFICE
CERTIFICATE OF CORRECTION

PATENT NO. : 6,764,988 B2 Page 1 of 1
APPLICATION NO. : 09/837628
DATED : July 20, 2004
INVENTOR(S) : David William Koenig et al.

It is certified that error appears in the above-identified patent and that said Letters Patent is hereby corrected as shown below:

Column 19, claim 66, line 24, "3.00" should read --100--.

Signed and Sealed this

Nineteenth Day of December, 2006

JON W. DUDAS
*Director of the United States Patent and Trademark Office*